United States Patent [19]

Griffith et al.

[11] Patent Number: 4,593,031

[45] Date of Patent: Jun. 3, 1986

[54] METHOD OF TREATING DEPRESSION

[75] Inventors: Robert W. Griffith, Basking Ridge; Jack Singer, Short Hills, both of N.J.

[73] Assignee: Sandoz, Inc., E. Hanover, N.J.

[21] Appl. No.: 741,708

[22] Filed: Jun. 5, 1985

Related U.S. Application Data

[63] Continuation of Ser. No. 574,188, Jan. 25, 1984, abandoned, which is a continuation-in-part of Ser. No. 475,050, Mar. 14, 1983, abandoned, which is a continuation-in-part of Ser. No. 360,463, Mar. 22, 1982, abandoned.

[51] Int. Cl.$^4$ .................... A61K 31/44; A61K 31/135
[52] U.S. Cl. .................................... 514/288; 514/649
[58] Field of Search ................................. 514/288, 649

Primary Examiner—Stanley J. Friedman
Attorney, Agent, or Firm—Gerald D. Sharkin; Robert S. Honor; Thomas O. McGovern

[57] ABSTRACT

This invention relates to a composition and method for potentiating the antidepressant effect of dibenzocycloheptadiene-type antidepressant agents, for example, nortriptyline, in the treatment of depression, especially geriatric depression, by administering them in combination with an approximately 1:1:1 by weight mixture of dihydroergocryptine (2:1 α:β), dihydroergocornine and dihydroergocristine.

18 Claims, No Drawings

METHOD OF TREATING DEPRESSION

This is a continuation of application Ser. No. 574,188, filed Jan. 25, 1984, now abandoned, which in turn is a continuation-in-part of Ser. No. 475,050, filed Mar. 14, 1983, now abandoned, which in turn is a continuation-in-part of Ser. No. 360,463, filed Mar. 22, 1982, now abandoned.

This invention relates to a method of potentiating the antidepressant effect of dibenzocycloheptadiene-type antidepressant agents, for example, nortriptyline, in the treatment of depression, especially geriatric depression, and in particular, senile dementia with depression, by administering them in combination with an essentially 1:1:1 by weight mixture of dihydroergocryptine (2:1α:β), dihydroergocornine and dihydroergocristine or a pharmaceutically acceptable acid addition salt thereof, which is referred to herein as the ergopeptide component.

This invention further relates to a composition useful in treating depression, in particular, geriatric depression, comprising a therapeutic effective amount of a dibenzocycloheptadiene antidepressant and a potentiating effective amount of the ergopeptide component. The composition is especially useful in treating senile dementia with depression, e.g., as defined by DMS-III Diagnostic Criteria, American Psychiatric Association (290.21) Diagnostic and Statistical Manual of Mental Disorders (Third Edition).

Depression is one of the most common psychiatric disturbances seen by the physician, especially in the elderly patient. The treatment of depression has generally been improved dramatically by the development of tricyclic antidepressive agents such as the benzocycloheptadiene-type antidepressants. Unfortunately, the therapeutic effect of such agents is often accompanied by troublesome side effects such as anticholinergic, cardiovascular and central nervous system (CNS) reactions. In the geriatric patient, these side effects are especially problematical, necessitating the use of lower daily doses of the antidepressant. At the lower doses, the effect of the drug is often less than that desired.

It has now been found that the effectiveness of benzocycloheptadiene antidepressants at lower dosage levels can be significantly enhanced by administering them in combination with the ergopeptide component above. The antidepressant of this invention is selected from the compounds of the formula

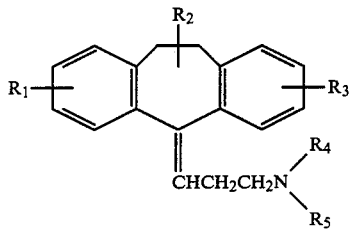

(I)

where $R_1$, $R_2$ and $R_3$ are each independently hydrogen, chloro or bromo, and $R_4$ and $R_5$ are each independently hydrogen, alkyl of 1 to 6 carbon atoms, benzyl or cycloalkyl of 3 to 8 carbon atoms, or a pharmaceutically acceptable acid addition salt thereof.

The preferred antidepressant agent is 5-(3-methylaminopropylidene)-10,11-dihydro-5H-dibenzo[a,d]cycloheptene, which is referred to herein as nortriptyline. The preferred salt form is the hydrochloride salt form.

The preferred ergopeptide component salts of this invention are the methanesulfonate salts of the 1:1:1 by weight mixture of dihydroergocryptine (2:1α:β), dihydrocornine and dihydroergocristine. The generic name of this mixture is ergoloid mesylates.

The compounds of formula (I) are normally administered in dosages ranging from 30 to 300 milligrams per day. The maintenance dosages range from 50 to 150 milligrams per day. In the adolescent and elderly patient, the dosage range is much lower, between 30 to 75 milligrams per day. It has now been found that when the compound of formula (I) is administered to the patient at a daily dosage of from 10 to 150, preferably 20 to 150, more preferably 30 to 150 milligrams most, preferably 30 to 75 milligrams, in combination with 1 to 10, preferably 2 to 10, more preferably 3 to 9 milligrams per day of the ergopeptide components, the response is essentially equivalent to that obtained with the higher doses of antidepressant. The preferred dosage of nortriptyline is 50 to 60 milligrams per day.

In an in-patient study, five patients ranging in age from 26 to 66 years suffering from depression and having a score of 19 to 30 on the Hamilton Depression Scale (A Rating Scale for Depression, M. Hamilton, Nerosurg. Psychiat. 23, 56–62, 1960) were given 20 milligrams of nortriptyline and 2 milligrams of ergoloid mesylate three times a day for 4 weeks. All five patients had a good response and improved significantly on the combination. The Hamilton Depression Scale score for each patient dropped below 8 and the onset of relief from the depression came much earlier than is normal with the antidepressant alone. Several patients noticed a significant improvement at the end of the first week. The incidence of side effects was very acceptable and their severity was minimal to mild. All five patients in the study felt they were getting effective treatment for their depression.

Similar results were obtained at the same dosage in a four center in-house study with 53 out of 60 patients, who began the study, ranging in age from 18 to 55 years. The investigators again noted that there was a rapid onset of action within the first week and a subsequent steady and continued improvement. Marked patient acceptance was indicated by the fact that only 7 patients dropped out of the study. Over 50% of the patients who completed the 28 days of treatment had complete remissions and final HAM-D scores equal to or less than 5. Blood plasma concentrations were at the extreme low end or below the therapeutic window for nortriptyline, which is 50 to 140 nanograms per milliliter of plasma. At 60 milligrams per day in the study, the blood plasma levels were 20 to 40 nanograms per milliliter, but the response of the patients was similar to that conventionally observed at the 100 nanogram level. The investigators were all pleased with the results and again the patients believed they were getting effective treatment.

For the antidepressant use, the compound of formula (I) and the ergopeptide component may be administered orally or parenterally as such or admixed with conventional pharmaceutical carriers. They may be combined in a single preparation or may be administered separately. They may be administered orally in such forms as tablets, dispersible powders, granules, capsules, syrups and elixirs, and parenterally as solutions, e.g., a sterile injectable aqueous solution. The composition for oral use may contain one or more conventional adjuvants, such as sweetening agents, flavoring agents, coloring agents and preserving agents, in order to provide an elegant and palatable preparation. Tablets may contain the active ingredients in admixture with conventional pharmaceutically acceptable excipients, e.g., inert diluents, such as calcium carbonate, sodium carbonate, lactose, and talc, granulating and disintegrating agents, e.g., starch and alginic acid, binding agents, e.g., starch gelatin and acacia, and lubricating agents, e.g., magnesium stearate, stearic acid and talc. The tablets may be uncoated or coated by known techniques to delay disintegration and adsorption in the gastrointestinal tract and thereby provide a sustained action over a longer period. Similarly, suspensions, syrups and elixirs may contain the active ingredients in admixture with any of the conventional excipients utilized in the preparation of such compositions, e.g., suspending agents such as methylcellulose, tragacanth and sodium alginate; wetting agents such as lecithin, polyoxyethylene stearate and polyoxyethylene sorbitan monooleate; and preservatives such as ethyl p-hydroxybenzoate. Capsules may contain the active ingredients alone or admixed with an inert solid diluent, e.g., calcium carbonate, calcium phosphate and kaolin. The injectable compositions are formulated as known in the art. These pharmaceutical preparations may contain up to about 90% of the active ingredients in combination with the carrier or adjuvant.

The preferred antidepressant, nortriptyline in hydrochloride salt form, is commercially available in a solution or capsule containing 10 milligrams of the active ingredient per unit dose. Similarly, the preferred potentiating agent of this invention, ergoloid mesylate, is also available commercially in tablet form containing one milligram of the active ingredient. The present invention may be carried out by administering two to three capsules of nortriptyline and two to three ergoloid mesylate tablets three times a day to the depressed patient.

EXAMPLE 1

Tablets and Capsules Suitable for Oral Administration

Tablets and capsules containing the ingredients indicated below may be prepared by conventional techniques and are useful in treating depression at a dose of one tablet or capsule one to three times a day.

| Ingredient | Weight (mg.) Tablet | Capsule |
|---|---|---|
| Nortriptyline HCl | 22.7* | 22.7 |
| Ergoloid mesylate | 2 | 2 |
| Tragacanth | 10 | — |
| Lactose | 172.8 | 225.3 |
| Corn Starch | 25 | — |
| Talcum | 15 | — |
| Magnesium Stearate | 2.5 | — |
| | 250 | 250 |

*Equivalent to 20 mg of nortriptyline base.

In analogous manner to that described above, capsules, tablets, suppositories, dispersible powders, syrups, elixirs, suspensions or solutions are made using conventional carriers and diluents for the desired formulation and are effective antidepressant preparations when administered enterally or parenterally as appropriate to a patient in need of such treatment.

What is claimed is:

1. An oral pharmaceutical composition useful in the treatment of depression or senile dementia with depression in humans comprising a compound of the formula

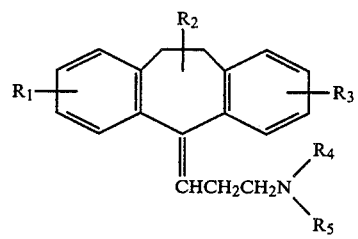

where $R_1$, $R_2$ and $R_3$ are each independently hydrogen, chloro or bromo; and $R_4$ and $R_5$ are each independently hydrogen, alkyl of 1 to 6 carbon atoms, benzyl or cycloalkyl of 3 to 8 carbon atoms, or a pharmaceutically acceptable acid addition salt thereof and an essentially 1:1:1 by weight mixture of dihydroergocryptine (2:1α:β), dihydroergocornine and dihydroergocristine or a pharmaceutically acceptable acid addition salt thereof and a pharmaceutically acceptable carrier therefor, said compound and said mixture being present in amounts sufficient to provide 10 to 150 milligrams of compound per day and 1 to 10 milligrams of mixture per day.

2. A pharmaceutical composition according to claim 1 comprising 30 to 75 milligrams of the compound.

3. A pharmaceutical composition according to claim 1 comprising 30 to 75 milligrams of nortriptyline in free base or pharmaceutically acceptable acid addition salt form and 3 to 9 milligrams of the mixture.

4. A pharmaceutical composition according to claim 3 comprising 50 to 60 milligrams of nortriptyline.

5. A composition according to claim 3 in which the compound is nortriptyline hydrochloride and the mixture is in the form of the mesylate salts.

6. The pharmaceutical composition of claim 5 comprising 22.7 milligrams of nortriptyline hydrochloride and 2 milligrams of the mesylate salts of the mixture per unit dosage.

7. The pharmaceutical composition of claim 6 in the form of a tablet.

8. A pharmaceutical composition according to claim 1 comprising 20 to 150 milligrams of the compound and 2 to 10 milligrams of the mixture.

9. The pharmaceutical composition according to claim 1 comprising 30 to 150 milligrams of the compound and 3 to 9 milligrams of the mixture.

10. A method for treating depression or senile dementia with depression in humans which comprises administering to a patient in need of said treatment 30 to 150 milligrams of a compound of the formula

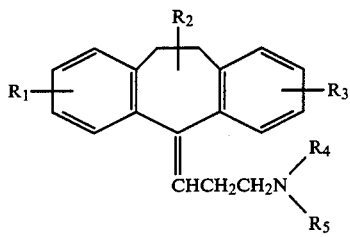

(I)

where $R_1$, $R_2$, $R_3$, $R_4$ and $R_5$ are as defined in claim 1 or a pharmaceutically acceptable acid addition salt thereof, and 3 to 9 milligrams of of an essentially 1:1:1 by weight mixture of dihydroergocryptine (2:1α:β), dihydrocornine and dihydroergocristine or a pharmaceutically acceptable acid addition salt thereof.

11. A method according to claim 8, wherein 30 to 75 milligrams of the compound is administered daily.

12. A method according to claim 8, wherein 30 to 75 milligrams of nortriptyline in free base or pharmaceutically acceptable acid addition salt form and 3 to 9 milligrams of the mixture are administered daily.

13. A method according to claim 11, wherein 50 to 60 milligrams of the compound is administered daily.

14. A method according to claim 11 in which the compound is nortriptyline hydrochloride and the mixture is in the form of the mesylate salts.

15. A method according to claim 13, wherein 22.7 milligrams of nortriptyline hydrochloride and 2 milligrams of the mesylate salts of the mixture are administered in a unit dosage form three times a day.

16. The method according to claim 14 in which the unit dosage form is a tablet.

17. A method for treating depression or senile dementia with depression in humans which comprises administering to a patient in need of said treatment 10 to 150 milligrams of a compound of the formula

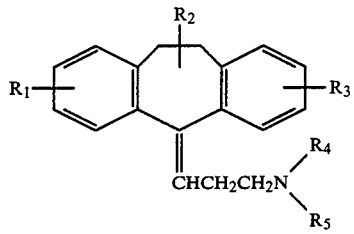

where $R_1$, $R_2$, $R_3$, $R_4$ and $R_5$ are as defined in claim 1 or a pharmaceutically acceptable acid addition salt thereof, and 1 to 10 milligrams of an essentially 1:1:1: by weight mixture of dihydroergocryptine (2:1α:β), dihydrocornine and dihydroergocristine or a pharmaceutically acceptable acid addition salt thereof.

18. A method according to claim 17, wherein 20 to 150 milligrams of the compound and 2 to 10 milligrams of the mixture are administered daily.

* * * * *